United States Patent [19]

Patterson

[11] Patent Number: 5,011,718
[45] Date of Patent: Apr. 30, 1991

[54] METHOD AND APPARATUS FOR REDUCING RESIDUAL LEVELS OF ETHYLENE OXIDE IN REPEATEDLY STERILIZED POLYMERIC DEVICES

[75] Inventor: William H. Patterson, Jacksonville, Tex.

[73] Assignee: Monarch Products, Inc., Jacksonville, Tex.

[21] Appl. No.: 189,972

[22] Filed: May 4, 1988

[51] Int. Cl.$^5$ ............................................. A61L 2/00
[52] U.S. Cl. .................... 428/35.7; 206/363; 220/367; 428/35.9; 422/310
[58] Field of Search .................. 428/35.8, 35.9, 35.7; 422/292, 310; 206/363; 220/367

[56] References Cited

U.S. PATENT DOCUMENTS

| | | | |
|---|---|---|---|
| 2,342,067 | 2/1944 | Turner | 21/91 |
| 3,410,395 | 11/1968 | Sellers | 229/3.5 |
| 3,454,189 | 7/1969 | Lauterbach | 220/97 |
| 3,750,827 | 8/1973 | Wick | 220/74 |
| 3,890,096 | 6/1975 | Nichol et al. | 21/105 |
| 3,946,872 | 3/1976 | Sturm | 206/498 |
| 4,121,714 | 10/1978 | Daly et al. | 206/363 |
| 4,210,674 | 7/1980 | Mitchell | 426/107 |
| 4,267,420 | 5/1981 | Brastad | 219/10.55 |
| 4,359,495 | 11/1982 | Schroeder et al. | 428/35 |
| 4,402,407 | 9/1983 | Maly | 206/363 |
| 4,416,906 | 11/1983 | Watkins | 426/107 |
| 4,457,977 | 7/1984 | Walles | 428/35.9 |
| 4,551,311 | 11/1985 | Lorenz | 422/300 |
| 4,617,178 | 10/1986 | Nichols | 422/310 |
| 4,792,042 | 12/1988 | Koehn et al. | 428/35.8 |
| 4,798,292 | 1/1989 | Hauze | 422/310 |

FOREIGN PATENT DOCUMENTS 2165754A 4/1986 United Kingdom.

Primary Examiner—James J. Seidleck
Attorney, Agent, or Firm—Baker & Botts

[57] ABSTRACT

A method for reducing the build-up of residual levels of ethylene oxide in a polymeric medical instrument sterilization container (32) is provided. The container (32) is electroplated in a tank (50) with successive layers of copper, nickel and chromium. The layers of copper, nickel and chromium provide a protective coating of material dense enough to prevent the ethylene oxide from penetrating to and being absorbed by the less dense polymeric container (32). Thus the polymeric container (32) may be repeatedly sterilized without a hazardous build-up of residual ethylene oxide.

7 Claims, 1 Drawing Sheet

METHOD AND APPARATUS FOR REDUCING RESIDUAL LEVELS OF ETHYLENE OXIDE IN REPEATEDLY STERILIZED POLYMERIC DEVICES

TECHNICAL FIELD OF THE INVENTION

This invention relates to the sterilization of medical devices, and more particularly to a method and apparatus for preventing build-up of residual levels of ethylene oxide in polymeric medical devices.

BACKGROUND OF THE INVENTION

The medical industry has begun to use more and more devices made from polymers, such as sterilization containers, proctoscopes, orthoscopes and neural scopes. Like other medical devices, polymeric devices must be sterilized before each use, and thus over their useful lifetime, the sterilization process is repeated many times over.

Typical sterilization processes include exposure to sterilants such as steam or ethylene oxide ($C_2H_4O$). Since exposure to steam is likely to deform a polymeric device, ethylene oxide is the sterilant most frequently used with polymeric devices. On the positive side, ethylene oxide is an excellent sterilant, but on the negative side, ethylene oxide is an extremely poisonous and highly flammable gas. Hospitals must either provide safe sites and procedures to conduct their own sterilizations using ethylene oxide or use a more expensive commercial sterilizing contractor.

Whether a hospital does its own sterilizing or uses a contractor, polymers, due to their low density, tend to absorb and retain ethylene oxide. The greater the number of sterilizations, the greater will be the amount of residual or absorbed ethylene oxide in a particular polymeric device.

The Federal Food and Drug Administration (FDA) has written regulations that delineate the maximum allowable amounts of residual ethylene oxide. Current FDA regulations restrict residual levels to 250 parts per million (ppm) of ethylene oxide. Unfortunately, polymeric devices tend to exceed this maximum allowable level of residual ethylene oxide after only a few sterilizations. Thus, there is a need for a method to reduce the build-up of residual levels of ethylene oxide in polymeric medical devices.

SUMMARY OF THE INVENTION

The present invention disclosed herein comprises a method and apparatus for reducing the build-up of residual levels of ethylene oxide in polymeric medical devices which substantially eliminates or reduces problems associated with such build-up The present invention allows repeated ethylene oxide sterilization cycles of polymeric devices without exceeding the Federal Food and Drug Administration (FDA) limitations.

In accordance with one aspect of the invention, a method of reducing residual levels of a sterilant in a polymeric device is provided. The polymeric device is placed in a coating apparatus and covered with a layer of a high density material such as nickel. The high density material prevents penetration of ethylene oxide to the polymeric device.

In another aspect of the present invention, portions of a sterile packaging system are electroplated with successive layers of copper, nickel and chrome. The electroplated portions are then assembled to form the sterile packaging system. It is a technical advantage of the present invention in that repeated sterilizations of polymeric devices are allowed without building residual levels of ethylene oxide beyond the allowed FDA limitations.

BRIEF DESCRIPTION OF THE DRAWINGS

For a more complete understanding of the present invention and for further advantages thereof, reference is now made to the following Detailed Description taken in conjunction with the accompanying Drawings in which.

DETAILED DESCRIPTION OF THE INVENTION

In the medical industry, instruments and other devices must be sterilized before use. Common ($C_2H_4O$, sterilization methods utilize ethylene oxide $C_2H_4O$, hereinafter ETO) or steam as the sterilant. ETO is used with polymeric instruments, since polymers such as, for example, acrylonitrile-butadiene styrene (ABS), polypropylene, urethane and epoxy resins, may melt or warp when exposed to heat. Since ETO is an extremely poisonous and flammable gas, it is frequently blended with another substance such as freon (a mixture commonly used comprises 12% ETO and 88% freon) to reduce the likelihood of an accident. As used herein, ETO designates any gas containing up to 100% ethylene oxide which is used as a sterilant.

Polymers, unfortunately, do not have a molecular structure that is dense enough to prevent absorption of ETO. ETO is thus absorbed into the molecular structure each time a polymeric device is sterilized, thereby resulting in a build-up of ETO. This residual ETO is slowly dissipated into the environment from the polymeric device where medical personnel or patients may be harmfully exposed. Typically, the polymeric device is reused and resterilized before all the residual ETO is dissipated, and, therefore, the residual levels continue to build to even higher levels.

The Federal Food and Drug Administration (FDA) has written safety regulations which delineates the maximum allowable residual levels of ETO at 250 parts per million (ppm). Additionally, OSHA has set their own regulations which are even more restrictive such as limiting exposure over any eight hour time frame to no more than 1 ppm and no more than 10 ppm per any 15 minute time frame. Depending upon the polymeric material and the concentration of the ETO used for sterilization, the residual levels in a medical device may exceed the maximum limit in a relatively few number of sterilizations. These strict limits require the introduction of a technique to prevent residual build-up of ETO.

Figure 1:
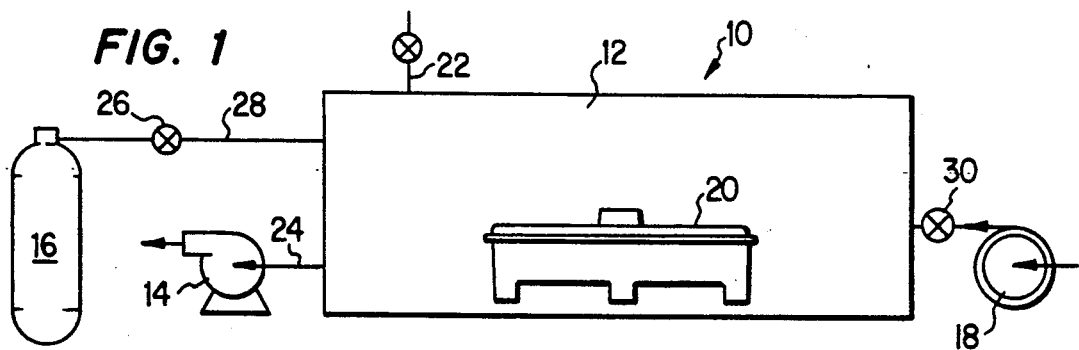
FIG. 1 is a cross-sectional view of a sterilizing apparatus which utilizes ethylene oxide.

In FIGS. 1-4, like items are identified by like and corresponding numerals for ease of reference. Referring to FIG. 1, a typical sterilizing apparatus is generally identified by reference numeral 10. The sterilizing apparatus 10 comprises a chamber 12 which is appropriately sealed, not shown, to allow the drawing of a vacuum therein. A vacuum pump 14 for evacuating chamber 12, and a pressurized tank 16 containing ETO are provided. A blower 18 is utilized to aerate an item 20 to be sterilized, and an exhaust port 22 allows removal of the sterilant during aeration of the item 20.

In operation, an item 20 to be sterilized, such as, for example, a medical instrument sterilization container, an orthoscope, or any other polymeric device, is placed within the chamber 12. A vacuum is then drawn within chamber 12 by vacuum pump 14 through connecting tube 24. A sterilant such as ETO is introduced to chamber 12 from tank 16 by opening valve 26 in connecting tube 28. The item 20 is sterilized by exposure to the ETO for a predetermined amount of time, for example, 1.5-3 hours.

After the required time, exhaust port 22 is opened and blower 18 is activated to force air through entrance port 30 into chamber 12 around item 20. The item 20 is allowed to aerate for 16-24 hours in an attempt to remove as much residual ETO as possible. Unfortunately, as stated previously, due to the low density of polymeric materials, the ETO remains in and is absorbed by the polymers constituting a continuing danger to both medical personnel and patients.

TEST I

To exemplify this problem of ETO absorption, a test was conducted utilizing equipment as described above, by Sterilization Technical Services, Inc., 7500 W. Henrietta Rd., P.O. Box 349, Rush, New York 14543 to detect the presence of residual ETO on polymeric substances. Three polymeric materials were selected for the test: ABS, polypropylene and an epoxy resin.

PROCEDURE

The materials were exposed to ten cycles of sterilization and aeration in a system similar to that shown in FIG. 1 utilizing the following parameters:

| | |
|---|---|
| Temperature | 130° F. ± 10° F. |
| Prevacuum | 24-26 in. Mercury |
| Humidity | 60% Relative Humidity, .5 hr dwell |
| Sterilant Gas | 12/88 Ethylene Oxide/ Dichlorodifluoromethane (freon) |
| Gas Pressure | 8 psig |
| Exposure Time to Sterilant | 2.5 hours |
| Aeration Time Between Sterilization Cycles | 16 hours |

Samples were evaluated for residual ethylene oxide by gas chromatography before any exposures to the sterilant and after 1, 5 and 10 exposures.

| | Results: | | |
|---|---|---|---|
| Number of Exposure/Aeration Cycles | ETO (ppm) ABS | ETO (ppm) Polypropylene | ETO (ppm) Expoxy |
| 0 | Less than 1 | Less than 1 | Less than 1 |
| 1 | 133.0 | 18.0 | 55.0 |
| 5 | 423.0 | 66.0 | 181.0 |
| 10 | 557.0 | 200.0 | 200.0 |

These tests clearly indicate that polymeric materials retain residual amounts of ETO, and that the residual amounts increase with the number of sterilizations. Thus, there is need for the invention herein disclosed to protect medical personnel and patients from residual ETO.

Figure 2:
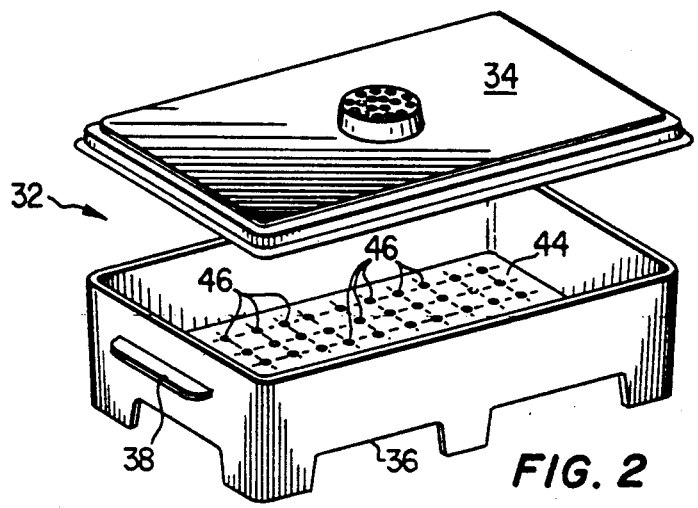
FIG. 2 is a perspective view of a sterile packaging system which may be coated in accordance with the preferred embodiment of the present invention.

Referring to FIGURE 2, a medical instrument sterilization container is generally identified by the reference numeral 32. The container 32 comprises a polymeric material such as, for example, ABS. While the present invention will be described with respect to container 32, it will be understood that a wide variety of medical devices can also utilize the present invention. For example, protoscopes, osthoscopes and many other polymeric devices may also be formed in accordance with the present invention.

The container 32 has a top 34 and a base section 36 which is provided with exterior handles 38 (only one of which is shown). A bottom portion 44 is provided with a plurality of holes 46 to allow passage therethrough of a sterilant. The container 32 is manufactured in sections which are prefabricated by injection molding techniques. A container especially designed for sterilization of medical instruments is disclosed in U.S. Pat. No 4,617,178, Oct. 14, 1986, to Nichols and is incorporated herein by reference.

After being formed by injection molding techniques, not shown, the polymeric sections such as top 34 are coated with a dense material. It is of primary importance to the present invention that the materials used to coat the sections comprise a material having a molecular structure dense enough to prevent the passage of ETO therethrough, such as, for example, chromium, copper or nickel. The dense materials may be applied to the polymeric sections by any appropriate method such as hot metal spraying, electroplating or vacuum metallizing, all of which are well known in the art.

Figure 3:
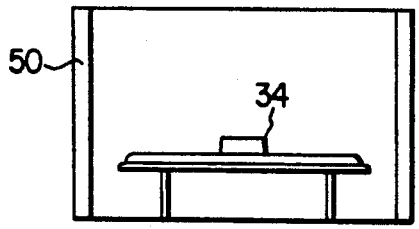
FIG. 3 is a cross-sectional view of an electroplating tank in accordance with the present invention.
Figure 4:
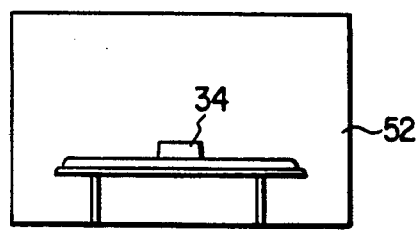
FIG. 4 is a cross-sectional view of a chemical bath tank in accordance with the present invention.

Referring to FIGS. 3 and 4, the top section 34 is coated by an electroplating device such as depicted by tank 50. In an electroplating device, the item to be plated, such as top section 34, is a cathode while the material to be plated which is suspended in a chemical solution known as a keeper is an anode. During the electroplating process, an electric current is passed through the chemical solution and the material to be plated is dissolved and electrodeposited on the cathode, in this case, the top section 34.

After the desired amount of plating has occurred, the top section 34 is placed in a separate tank 52 (FIG. 4) to be washed. The wash material in tank 52 comprises a cleaning bath such as, for example, alcohol or acetone. The cleaning bath removes all residue from the electroplating process in order to prevent contamination of any subsequent electroplating, if desired. It is only necessary to deposit as little as a monolayer of the dense material over the polymer to prevent passage of the ETO therethrough. However, it is allowable to apply as thick a layer of the dense material as desired as long as the functionality of the polymeric device is not impaired. Therefore, an inflexible device, such as a medical instrument sterilization container, may be coated with multiple layers, whereas a flexible device such as an orthoscope would likely allow only a relatively thin coating.

TEST II

A test was conducted utilizing the same parameters and equipment as in TEST I above of ABS samples coated in accordance with the present invention compared with ABS samples without coating. The samples were removed after the first and 10th sterilization/aeration cycle and evaluated for ETO residuals by gas chromotography. The results were as follows:

| Number of Exposure/Aeration Cycles | ETO (ppm) Coated | ETO (ppm) Non-coated |
| --- | --- | --- |
| 1 | Less than 1 | 162 |
| 10 | Less than 1 | 211 |

This test clearly demonstrates that coating the polymeric material with a dense covering greatly reduces the build-up of residual levels of ETO. Thus, medical personnel and patients are protected from the hazardous effects of residual ETO.

Although the present invention has been described with respect to a specific preferred embodiment thereof, various changes and modifications may be suggested to one skilled in the art, and it is intended that the present invention encompass such changes and modifications as fall within the scope of the appended claims.

What is claimed is:

1. A medical device capable of being repeatedly sterilized with ethylene oxide without warping or melting and without build-up of residual levels of ethylene oxide therein, comprising:

a polymeric base having generally rigid sides dimensioned for receiving medical instruments and apertures for allowing ethylene oxide to pass through said polymeric base;

a polymeric lid for covering said polymeric base to define a polymeric container for medical instruments; said lid having an aperture therein to allow passage of ethylene oxide, wherein ethylene oxide comes in contact with both the exterior and interior surfaces of said container; and a coating of dense material formed over the interior and exterior surfaces of said polymeric base and said polymeric lid, said coating having the characteristic of inhibiting penetration of the interior and exterior surfaces of said polymeric base and said polymeric lid by the ethylene oxide, thereby reducing build-up of residual levels of the ethylene oxide on the interior and exterior surfaces of said polymeric base and said polymeric lid.

2. The device of claim 1, wherein said polymeric base and said polymeric lid comprise acrylonitrile-butadiene styrene.

3. The device of claim 1, wherein said polymeric base and said polymeric lid comprise polypropylene.

4. The device of claim 1, wherein said dense material comprises a substance sufficiently dense to prevent penetration of ethylene oxide.

5. The device of claim 4, wherein said dense material comprises copper.

6. The device of claim 4, wherein said dense material comprises nickel.

7. The device of claim 4, wherein said dense material comprises chromium.

* * * * *